(12) United States Patent
Takachiyo et al.

(10) Patent No.: US 11,229,584 B2
(45) Date of Patent: *Jan. 25, 2022

(54) PIGMENT DISPERSION LIQUID FOR COSMETICS, AND AQUEOUS LIQUID COSMETIC USING SAME

(71) Applicant: MITSUBISHI PENCIL COMPANY, LIMITED, Tokyo (JP)

(72) Inventors: Keiichiro Takachiyo, Fujioka (JP); Satoshi Sakuma, Fujioka (JP)

(73) Assignee: MITSUBISHI PENCIL COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/979,573

(22) PCT Filed: Mar. 8, 2019

(86) PCT No.: PCT/JP2019/009456
§ 371 (c)(1),
(2) Date: Sep. 10, 2020

(87) PCT Pub. No.: WO2019/176800
PCT Pub. Date: Sep. 19, 2019

(65) Prior Publication Data
US 2021/0007946 A1  Jan. 14, 2021

(30) Foreign Application Priority Data
Mar. 12, 2018 (JP) .............................. JP2018-044347

(51) Int. Cl.
*A61K 8/04* (2006.01)
*A61K 8/34* (2006.01)
*A61K 8/41* (2006.01)
*A61K 8/81* (2006.01)
*A61Q 5/10* (2006.01)

(52) U.S. Cl.
CPC ................ *A61K 8/04* (2013.01); *A61K 8/34* (2013.01); *A61K 8/415* (2013.01); *A61K 8/8152* (2013.01); *A61Q 5/10* (2013.01); *A61K 2800/4324* (2013.01)

(58) Field of Classification Search
CPC ... A61Q 5/10; A61Q 1/02; A61Q 1/10; A61K 8/19; A61K 8/34; A61K 8/817; A61K 2800/43; A61K 2800/432; A61K 8/04; A61K 8/044; A61K 8/8152; A61K 2800/59
USPC ...................................................... 424/70.1
See application file for complete search history.

(56) References Cited

U.S. PATENT DOCUMENTS

| | | | |
|---|---|---|---|
| 2003/0091521 A1* | 5/2003 | Midha | A61K 8/0241 424/70.1 |
| 2003/0165449 A1* | 9/2003 | Kaczvinsky, Jr. | A61P 27/02 424/70.1 |
| 2008/0038218 A1* | 2/2008 | Brun | A61Q 5/065 424/70.16 |
| 2008/0234392 A1 | 9/2008 | Ehara et al. | |
| 2010/0104610 A1* | 4/2010 | Dueva-Koganov | A61Q 1/06 424/401 |
| 2010/0152135 A1* | 6/2010 | Blin | A61K 8/922 514/63 |
| 2010/0172858 A1* | 7/2010 | Jegou | A61Q 5/12 424/70.16 |
| 2015/0007845 A1* | 1/2015 | Teboul | A45D 19/02 132/200 |
| 2015/0164196 A1* | 6/2015 | Teboul | A45D 19/00 132/208 |
| 2015/0174051 A1* | 6/2015 | Teboul | A61K 8/26 424/70.6 |
| 2015/0297481 A1* | 10/2015 | Wahler | A61Q 5/08 424/401 |

FOREIGN PATENT DOCUMENTS

| | | |
|---|---|---|
| JP | H09208436 A | 8/1997 |
| JP | H10273431 A | 10/1998 |
| JP | 2001181128 A | 7/2001 |
| JP | 2008063251 A | 3/2008 |
| JP | 2008308435 A | 12/2008 |
| JP | 2017119797 A | 7/2017 |
| JP | 2018058775 A | 4/2018 |
| WO | 2007063902 A1 | 6/2007 |

OTHER PUBLICATIONS

International Search Report (PCT/ISA/210) dated Jun. 4, 2019, by the Japan Patent Office as the International Searching Authority for International Application No. PCT/JP2019/009456 and an English translation of the Report. (5 pages).

Written Opinion (PCT/ISA/237) dated Jun. 4, 2019, by the Japan Patent Office as the International Searching Authority for International Application No. PCT/JP2019/009456. (5 pages).

* cited by examiner

*Primary Examiner* — Eisa B Elhilo
(74) *Attorney, Agent, or Firm* — Buchanan, Ingersoll & Rooney PC

(57) ABSTRACT

Provided are a pigment dispersion liquid for cosmetics having excellent dispersibility for a pigment of Pigment Red 4 (C.I. 12085) and aging stability, and an aqueous liquid cosmetic using the same, which is suitable for hair dyes and the like. The pigment dispersion liquid for cosmetics contains, at least, water, a water-soluble organic solvent, a pigment of Pigment Red 4 (C.I. 12085), and a (methacryloyl ethylbetaine/acrylates) copolymer, and a ratio of the water to total solvents is 30 to 95% by mass.

15 Claims, No Drawings

PIGMENT DISPERSION LIQUID FOR COSMETICS, AND AQUEOUS LIQUID COSMETIC USING SAME

TECHNICAL FIELD

The present invention relates to a pigment dispersion liquid for cosmetics having excellent dispersibility for a pigment of Pigment Red 4 (C.I. 12085, Japanese legal dye: Red No. 228) and aging stability, and an aqueous liquid cosmetic using the same.

BACKGROUND ART

Since pigments have excellent masking properties and color development, many pigment-containing materials have been used as colorants for cosmetics such as temporary hair dyes and makeup cosmetics. In addition, amphoteric polymer resins are often used as resins to be added into cosmetics such as hair dyes.

Pigment Red 4 (Red No. 228), which is a pigment, is generally called "Permaton Red" (C.I. 12085, D & C Red 36) and is used in colorants for cosmetic compositions such as makeup cosmetics and hair dyes. However, the dispersion liquid thereof requires a long time for dispersing, and, at present, the dispersion liquid has problems such as low productivity and poor aging stability in the manufacture of the dispersion liquid.

On the other hand, for example, the following related art documents 1) to 5) which refer to dispersibility and aging stability in liquid cosmetics containing a pigment are known.

1) A coloring hair cosmetic including water as a main solvent, an acrylic amphoteric polymer resin having a specific structure, an acidic dye, and carbon black is disclosed (for example, see Patent Document 1). The acrylic amphoteric polymer resin thereof forms a robust resin coating on the hair, while the poor hair washing performances thereof and strong stiffness have been pointed out as problems. Furthermore, when a dye and a pigment are used in combination, it is known that the viscosity of the cosmetic itself disadvantageously tends to increase in aging.

2) A temporary hair dye including an alcohol having 4 or less carbon atoms as main solvent, an N-methacryloylethyl-N,N-dimethylammonium.α-N-methylcarboxybetaine.butyl methacrylate copolymer of an acrylic amphoteric polymeric resin as a dispersant, and titanium black as a coloring component is disclosed (for example, see Patent Document 2). Here, in addition to titanium black, Red No. 228 (C.I. 12085) is disclosed as a pigment that may be added. In this case, an increase in the viscosity or the like is seemingly suppressed, yet Patent Document 2 does not specifically refer to the addition of an organic pigment such as Pigment Red 4 (C.I. 12085: Red No. 228).

3) A temporary hair dye including ethanol as a main solvent, black titanium oxide, a (methacryloyloxy ethylcarboxybetaine/alkyl methacrylate) copolymer, hydroxypropyl cellulose, and glycerin is disclosed (for example, see Patent Document 3). Patent Document 3 also indicates Pigment Red 4 (C.I. 12085: Red No. 228) as a pigment that may be added in addition to titanium black. In the case of this document, the viscosity of the cosmetic measured with a B-type viscometer is relatively high to very high, i.e., from 50 to 30,000 mPa·sec, and this document indicates examples in which Pigment Red 57 (C.I. 15850: Red No. 202) and Pigment Yellow 1 (C.I. 11680: Yellow No. 401) are contained, yet the document does not specifically refer to the addition of Pigment Red 4 (C.I. 12085: Red No. 228).

4) A hair coloring composition which contains a branched polyglycerin-modified silicone having a specific structure, a betaine-modified silicone, and a film-forming resin, and may also contain an organic pigment is disclosed (for example, see Patent Document 4). Also, this document exemplifies the use of a (methacryloyloxy ethylcarboxybetaine/alkyl methacrylate) copolymer in combination with Acid Black 1 (C.I. 20470: Black No. 401), Acid Violet No. 43 (C.I. 60730: Violet No. 401), and Acid Orange 7 (C.I. 15510: Orange No. 205), but does not especially refer to the addition of Pigment Red 4 (C.I. 12085: Red No. 228).

5) A liquid cosmetic containing sepiomelanin, an amphoteric compound, and water is disclosed (for example, see Patent Document 5). This document indicates an example in which this liquid cosmetic contains water as a main solvent and YUKAFORMER™ ((methacryloyloxy ethylcarboxybetaine/alkyl methacrylate) copolymer) for the dispersion of sepiomelanin, yet the document does not specifically refer to the addition of an organic pigment including Pigment Red 4 (C.I. 12085, Red No. 228).

CONVENTIONAL ART DOCUMENT

Patent documents

Patent Document 1: Japanese Patent Application Laid-Open No. Hei. 10-273431 (Claims, Examples and others, and Abstract)

Patent Document 2: Japanese Patent Application Laid-Open No. Hei. 9-208436 (Claims, Paragraph [0012], and others)

Patent Document 3: Japanese Patent Application Laid-Open No. 2008-63251 (Claims, Paragraph [0028], and others)

Patent Document 4: Japanese Patent Application Laid-Open No. 2008-308435 (Claims, Examples, and others)

Patent Document 5: Japanese Patent Application Laid-Open No . 2001-181128 A (Claims, Examples and others, and Abstract)

SUMMARY OF THE INVENTION

Problems to be Solved by the Invention

The present invention is to solve the above problems, and an object thereof is to provide a pigment dispersion liquid for cosmetics having excellent dispersibility for a pigment of Pigment Red 4 (C.I. 12085, Red No. 228) and aging stability, and an aqueous liquid cosmetic using the same, which is suitable for hair dyes and the like.

Means to Solve Problems

As a result of dedicated study on the above problems, the present inventors found that, by incorporating at least water, a water-soluble organic solvent, a pigment of Pigment Red 4 (C.I. 12085, Red No. 228), and a specific component, and setting a ratio of the water to total solvents to be within a specific range, the aforementioned pigment dispersion liquid for cosmetics and aqueous liquid cosmetic using the same, which is suitable for hair dyes and the like, are obtained, and completed the present invention.

Specifically, the pigment dispersion liquid for cosmetics of the present invention includes at least water, a water-soluble organic solvent, a pigment of Pigment Red 4 (C.I. 12085, Red No. 228), and a (methacryloyl ethylbetaine/acrylates) copolymer, and is also characterized in that a ratio of the water to total solvents is 30 to 95% by mass.

The water-soluble organic solvent is preferably a lower alcohol having 5 or less carbon atoms.

The lower alcohol is preferably ethanol.

The aqueous liquid cosmetic of the present invention contains the pigment dispersion liquid for cosmetics described above.

The aqueous liquid cosmetic preferably has a ratio of the water to total solvents 30 to 95% by mass.

In the aqueous liquid cosmetic, the lower alcohol having 5 or less carbon atoms is preferably contained besides the water.

The lower alcohol of the aqueous liquid cosmetic is preferably ethanol.

Advantageous Effects of Invention

The present invention provides a pigment dispersion liquid for cosmetics having excellent dispersibility for a pigment of Pigment Red 4 (C.I. 12085, Red No. 228) and aging stability, and an aqueous liquid cosmetic using the same, which is suitable for hair dyes and the like.

DESCRIPTION OF EMBODIMENTS

Hereinafter, embodiments of the present invention will be described in detail.

The pigment dispersion liquid for cosmetics of the present invention contains at least water, a water-soluble organic solvent, a pigment of Pigment Red 4 (C.I. 12085), and a (methacryloyl ethylbetaine/acrylates) copolymer, and is also characterized in that a ratio of the water to total solvents is 30 to 95% by mass.

The pigment of Pigment Red 4 (C.I. 12085, D & C Red 36) used in the present invention is a colorant (Red No. 228) that is listed in the legally approved dyes, and is commonly used in cosmetics in Japan. This pigment is a red powder and is generally called "Permaton Red" (D & C Red 36) [1-(2-chloro-4-nitrophenylazo)-2-naphthol ($C_{16}H_{10}ClN_3O_3$: molecular weight 327.72).

An aqueous dispersion liquid of Pigment Red 4 (C.I. 12085) needs a long dispersion time, and has problems such as low productivity and aging stability in the manufacture of the dispersion liquid, yet the problems thereof will be overcome by preparing a dispersion liquid with the blending characteristics according to the present invention.

The content of Pigment Red 4 (C.I. 12085) used is preferably 1 to 32% by mass, more preferably 2 to 25% by mass, based on the total amount of the pigment dispersion liquid for cosmetics, from the perspective of stability after dispersion and convenience in the manufacture of the cosmetics.

Setting the content of Pigment Red 4 (C.I. 12085) to 1% by mass or greater leads to excellent productivity and coloration properties when the pigment dispersion liquid is added to cosmetics. Moreover, when the content is set to 32% by mass or less, that leads to even better dispersibility and aging stability.

The water-soluble organic solvent for the present invention is used as a solvent for the pigment dispersion liquid for cosmetics, and examples thereof include lower alcohols having 5 or less carbon atoms. A specific example of the water-soluble organic solvent is at least one (alone or a mixture of two or more) of: methyl alcohol (methanol), ethyl alcohol (ethanol), n-propyl alcohol, isopropyl alcohol, n-butyl alcohol, sec-butyl alcohol, tert-butyl alcohol, isobutyl alcohol, pentyl alcohol, ethylene glycol, propylene glycol, and the like.

In particular, it is desired to use ethyl alcohol (ethanol), from the perspective of safety, handleability, and the like.

The content of the water-soluble organic solvent used is preferably 1.0 to 60.0% by mass, more preferably 5.0 to 30.0% by mass based on the total amount of the pigment dispersion liquid for cosmetics, from the perspective of stability, in a dissolved state, of the (methacryloyl ethylbetaine/acrylates) copolymer which will be described below, and, additionally, pigment dispersion stability, especially, stability at low temperatures.

By setting the content of the water-soluble organic solvent to 1.0% by mass or more, it is possible to achieve the effect of preventing the solvent from freezing at low temperatures and an antiseptic effect though slight. On the other hand, by setting the content to 60.0% by mass or less, the stability in a dissolved state of the (methacryloyl ethylbetaine/acrylates) copolymer is further improved as described below.

The (methacryloyl ethylbetaine/acrylates) copolymer for the present invention is a component which improves the dispersibility of Pigment Red 4 (C.I. 12085) and the aging stability when used to prepare a dispersion liquid.

This (methacryloyl ethylbetaine/acrylates) copolymer is a copolymer of two or more monomers composed of acrylic acid, methacrylic acid, or a simple ester thereof and methacryloyl ethylbetaine, which is generally called N-methacryloyloxyethyl-N,N-dimethylammonium-α-N-methylcarboxybetaine.alkyl methacrylate copolymer, and has a betaine unit in the polymer structure, and a polymer with the betaine unit exhibits specific behaviors different from behaviors of the other ionic polymers.

The (methacryloyl ethylbetaine/acrylates) copolymer is a component that has been heretofore used as a film-forming agent or a hairstyling agent, but, in the case of the present invention, is a component that provides novel applications as a component which improves the dispersibility of Pigment Red 4 (C.I. 12085) and the aging stability when used to prepare a dispersion liquid.

The (methacryloyl ethylbetaine/acrylates) copolymer that can be used include, among commercially available products, RAM Resin-1000 (manufactured by Osaka Organic Chemical Industry Ltd.) and Plascize L-440 (manufactured by Goo Chemical Co., Ltd.).

The content of the (methacryloyl ethylbetaine/acrylates) copolymer used is preferably 3.0 to 15.0% by mass, more preferably 5.0 to 10.0% by mass, in terms of solid content, based on the total amount of the pigment dispersion liquid for cosmetics, from the perspective of achieving excellent dispersibility of Pigment Red 4 (C.I. 12085) and excellent aging stability when it is used to prepare a dispersion liquid.

By setting the content of the (methacryloyl ethylbetaine/acrylates) copolymer to 3.0% by mass or more, the dispersion state of the pigment is stabilized, and the binding of the pigment or the like when blended into a cosmetic is improved. On the other hand, by setting the content to 15.0% by mass or less, the increase in viscosity is suppressed so that the convenience in the manufacture of the cosmetic is further improved.

In the present invention, the blending ratio between Pigment Red 4 (C.I. 12085) and the (methacryloyl ethylbetaine/acrylates) copolymer used is desirably set to a mass ratio of Pigment Red 4 (C.I. 12085) to the (methacryloyl ethylbetaine/acrylates) copolymer of 1:1 to 4:1, and is particularly preferably 2:1 to 4:1.

By setting the ratio to 1:1 to 4:1, a pigment dispersion liquid for cosmetics achieving both excellent dispersibility of Pigment Red 4 (C.I. 12085) and excellent aging stability can be obtained.

Water used as a solvent for the present invention can be distilled water, ion exchanged water, purified water, pure water, ultrapure water, or the like, and a ratio of water to total solvents (a total of water and water-soluble organic solvent) needs to be 30 to 95% by mass (0.30 to 0.95), and is preferably 60 to 95% by mass.

When the ratio of water to total solvents is less than 30% by mass (0.30), the aging stability becomes unstable, and the pigment cannot be dispersed. On the other hand, when the ratio exceeds 95% by mass (0.95), no pigment dispersion liquid for cosmetics can be manufactured due to the solvent, other than water, originally contained in each of the components.

The pigment dispersion liquid for cosmetics of the present invention contains the water-soluble organic solvent, Pigment Red 4 (C . I . 12085), (methacryloyl ethylbetaine/acrylates) copolymer, and water as described above, but a pH modifier, a surfactant, a viscosity modifier, a chelating agent, and the like can be appropriately used according to need, from the perspective of further improvement in dispersibility and stability in a dissolved state of each of the components.

Furthermore, the pigment dispersion liquid for cosmetics of the present invention can be prepared by blending the water-soluble organic solvent, Pigment Red 4 (C.I. 12085), (methacryloyl ethylbetaine/acrylates) copolymer, water, and other components as described above within the content ranges as described above, and homogeneously stirring and mixing the components.

For example, the pigment dispersion liquid for cosmetics can be prepared by stirring Pigment Red 4 (C . I . 12085), a water-soluble solvent, and a solvent such as water with a general purpose disperser or the like until homogeneous, mixing a (methacryloyl ethylbetaine/acrylates) copolymer therewith, and then further stirring the components with a disperser or the like using a homomixer or the like until homogeneous.

The thus-configured pigment dispersion liquid for cosmetics of the present invention can solve the problems of the long dispersion time needed for Pigment Red 4 (C.I. 12085) as a pigment in the dispersion liquid and low aging stability, and provides a pigment dispersion liquid for cosmetics having excellent dispersibility of Pigment Red 4 (C.I. 12085) and aging stability.

The obtained pigment dispersion liquid for cosmetics is suitably used in applications of cosmetics containing Pigment Red 4 (C.I. 12085), and preferred examples thereof include skin care cosmetics, scalp hair cosmetics, antiperspirant cosmetics, makeup cosmetics, ultraviolet light blocking cosmetics, and nail cosmetics. For example, there are indicated skin care cosmetics such as milky lotion, creams, lotions, sunscreen agents, suntan agents, antiacne cosmetics and essences, makeup cosmetics such as foundations, eye shadows, eyeliner cosmetics, eyebrow cosmetics, mascaras, blusher, nail colors, treatment nails, various gel nails, and lipsticks, rinses, conditioners, hair colors, set agents, hair restorers, deodorants, fragrances, and the like. In addition, the form of the product is not particularly limited, but the product can be applied to aqueous products such as liquids, emulsions, creams, pastes, gels, mousses, and sprays, because it is a dispersion liquid (aqueous).

In particular, the pigment dispersion liquid for cosmetics of the present invention is preferably used in aqueous liquid cosmetics such as hair dyes (including eyeliner cosmetics and mascaras) and aqueous nail colors due to the dispersion characteristics thereof.

As a specific embodiment of the aqueous liquid cosmetic of the present invention, the use thereof in a hair dye will be described below.

Examples of the hair dye that can be used include containing thereof, at least, the pigment dispersion liquid for cosmetics containing Pigment Red 4 described above (C . I . 12085) and general purpose hair dye components such as a resin, a lower alcohol, a hair dyeing aid, a pH modifier, and water. The hair dye can further contain a colorant other than Pigment Red 4 (C.I. 12085) described above according to the color variation of the hair dye, as needed.

The content of the pigment dispersion liquid for cosmetics containing Pigment Red 4 (C.I. 12085) described above is preferably 0.5 to 30.0% by mass, more preferably 1.0 to 25.0% by mass based on the total amount of the hair dye, from the perspective of hair dyeing effect, solubility, storage stability, and the like.

Colorants other than Pigment Red 4 (C.I. 12085) that can be used are dyes generally used in hair dyes, and examples thereof include inorganic pigments such as carbon black, black titanium oxide, yellow iron oxide, black iron oxide, red iron oxide, ultramarine blue, iron blue, chromium oxide, chromium hydroxide, carmine, and shikonin, and organic pigments such as barium, calcium, zirconium or aluminum lake pigments of water-soluble dyes such as Red No. 2 (Acid Red 27: C . I . 16185) , Red No. 3 (Acid Red 51: C. I. 45430) , Red No. 102 (Acid Red 18: C. I. 16255) , Red No. 104 (1) (Acid Red 92: C.I. 45410), Red No. 105 (1) (Acid Red 94: C.I. 45440), Red No. 106 (Acid Red 52: C.I. 45100), Red No. 227 (Acid Red 33: C.I. 17200), Red No. 230 (1) and Red No. 230 (2) (both Acid Red 87: C.I. 45380), Red No. 231 (Acid Red 92: C.I. 45410), Red No. 232 (Acid Red 94: C.I. 45440), Yellow No. 4 (Acid Yellow 23: C.I. 19140), Yellow No. 5 (Food Yellow 3: C.I. 15985), Yellow No. 202 (1) and Yellow No. 202 (2) (both Acid Yellow 73: C.I. 45350), Yellow No. 203 (Acid Yellow 3: C.I. 47005), Green No. 3 (Food Green: C.I. 42053), Green No. 201 (Acid Green 25: C.I. 61570), Green No. 204 (Solvent Green 7: C.I. 59040), Green No. 205 (Acid Green 5: C.I. 42095), Blue No. 1 (Food Blue 2: C.I. 42090), Blue No. 2 (Acid Blue 74: C.I. 73015), Blue No. 202 (Acid Blue 5: C.I. 42052), Blue No. 205 (Acid Blue 9: C.I. 42090), Orange No. 205 (Acid Orange 7: C.I. 15510), Orange No. 207 (Acid Red 95: C.I. 45425), and Brown No. 201 (Acid Orange 24: C.I. 20170); Red No. 201 (Pigment Red 57-1: C.I. 15850), Red No. 202 (Pigment Red 57: C.I. 15850), Red No. 203 (Pigment Red 53: C.I. 15585), Red No. 204 (Pigment Red 53 (Ba): C.I. 15585), Red No. 205 (Pigment Red 49 (Na): C.I. 15630), Red No. 206 (Pigment Red 49 (Ca): C.I. 15630), Red No. 207 (Pigment Red 49 (Ba): C.I. 15630), Red No. 208 (Pigment Red 49 (Sr): C.I. 15630), Red No. 215 (Solvent Red 49: C.I. 45170), Red No. 218 (Solvent Red 48: C.I. 45410), Red No. 219 (Pigment Red 64: C.I. 15800), Red No. 220 (Pigment Red 63 (Ca): C.I. 15880), Red No. 221 (Pigment Red 3: C.I. 12120), Red No. 223 (Solvent Red 43: C.I. 45380), Red No. 225 (Solvent Red 23: C.I. 26100), Red No. 226 (Vat Red 1: C.I. 73360), Yellow No. 201 (Acid Yellow 73: C.I. 45350), Yellow No. 204 (Solvent Yellow 33: C.I. 47000), Yellow No. 205 (Pigment Yellow 12: C.I. 21090), Green No. 202 (Solvent Green 3: C.I. 61565), Blue No. 201 (Vat Blue 1: C.I. 73000), Blue No. 204 (Vat Blue 6: C.I. 69825), Blue No. 404 (Pigment Blue 15: C.I. 74160), Orange No. 201 (Solvent Red 72: C.I. 45370), Orange No. 203 (Pigment Orange 5: C.I. 12075), Orange No. 204

(Pigment Orange 13: C.I. 21110), Orange No. 206 (Solvent Red 73: C.I. 45425), Orange No. 401 (Pigment Orange 1: C.I. 11725), Orange No. 402 (Acid Orange 20: C.I. 14600), Orange No. 403 (Solvent Orange No. 2: C.I. 12100, Black No. 401 (Acid Black 1: C.I. 20470), and Violet 201 (Solvent Violet 13: C.I. 60725). At least one of these colorants can be used.

When these colorants are used, the colorants are to be used in an amount 0.1 to 25.0% by mass based on the total amount of the hair dye from the perspective of hair dyeing effect, solubility, storage stability, and the like.

The resin that can be used is, for example, a resin having water resistance when dried or a resin having a film forming property, and an example thereof is at least one of (methacryloyloxy ethylcarboxybetaine/alkyl methacrylate) copolymers, (octylacrylamide/hydroxypropyl acrylate/butylaminoethyl methacrylate) copolymers, (hydroxyethyl acrylate/butyl acrylate/methoxyethyl acrylate) copolymers, N-methacryloylethyl-N,N-diemethylammonium.α-N-methylcarboxybetaine.butyl methacrylate copolymers, and (methacryloyl ethylbetaine/acrylates) copolymers.

These resins are preferably used in an amount 0.1 to 10.0% by mass, preferably 0.5 to 5.0% by mass, in terms of solid content, based on the total amount of the hair dye, from the perspective of water resistance, texture after application to the hair, coatability, and the like.

The lower alcohol that can be used can be preferably used from the perspective of low temperature stability, drying property, low irritation, and the like. Examples of the lower alcohol used include lower alcohols having 5 or less carbon atoms. A specific example of the lower alcohol is at least one (alone or as a mixture of two or more) of methyl alcohol (methanol), ethyl alcohol (ethanol), n-propyl alcohol, isopropyl alcohol, n-butyl alcohol, sec-butyl alcohol, tert-butyl alcohol, isobutyl alcohol, pentyl alcohol, and the like.

In particular, it is desired to use ethyl alcohol (ethanol), from the perspective of safety, handleability, and the like.

These lower alcohols are preferably used in an amount 10 to 80% by mass, more preferably 15 to 70% by mass, particularly preferably 15% to 65% by mass, based on the total amount of the hair dye.

The hair dyeing aid that can be used is used for further improvement of the hair dyeing effect, and is, for example, at least one of benzyl alcohol, phenylethyl alcohol, phenoxy ethanol, propylene carbonate, propylene glycol, ethoxydiglycol, N-methylpyrrolidone, N-methyl-2 pyrrolidone, and the like.

These hair dyeing aids are preferably used in an amount 2.0 to 20.0%, more preferably 5.0 to 15.0%, and particularly preferably 3.0 to 5.0%, based on the total amount of the hair dye, from the perspective of further hair dyeing effect and the prevention of color migration.

The pH modifier that can be used is for improving coloration properties, preventing skin irritation, and preventing skin dyeing troubles, and the pH of the hair dye is modified to preferably 2 to 5, and more preferably 3.5 to 5.0 by this pH modifier.

Examples of the pH modifier that can be used include organic acids and inorganic acids such as formic acid, acetic acid, lactic acid, tartaric acid, malic acid, citric acid, and glycolic acid, or salts thereof. In some cases, an alkali such as triethanolamine can be used.

The balance of the hair dye is adjusted with water (purified water, distilled water, ion exchanged water, pure water, tap water, etc.).

As the water content, the ratio of water to total solvents (a total of water and water-soluble organic solvent) is set preferably within the range 30 to 95% by mass (0.30 to 0.95), more preferably within the range 30 to 80% by mass.

In a case where the ratio of water to total solvents is less than 30% by mass (0.30), the aging stability will be poor, and the stability, in a dissolved state, of the water-soluble component when added will be bad. On the other hand, if the ratio exceeds 95% by mass (0.95), the possibility of inferior antimicrobial properties will be increased.

The thus-configured hair dye contains, at least, the pigment dispersion liquid for cosmetics containing Pigment Red 4 (C.I. 12085), resin, lower alcohol, hair dyeing aid, and pH modifier as described above. However, the hair dye can appropriately contain other materials within ranges that do not impair the effects of the present invention, for example, thickeners, various surfactants, preservatives, UV absorbers, antioxidants, anti-reduction agents, chelating agents, oily components, perfumes, and animal/plant extracts.

Examples of the thickener that can be used include cellulose thickeners such as hydroxyethyl cellulose, hydroxypropylmethyl cellulose, stearoxyhydroxypropylmethyl cellulose, hydroxypropylguar hydroxypropyltrimonium chloride, and cationized cellulose in which a cationic functional group is added to cellulose, resin thickeners such as polyvinyl alcohol and acrylic acid, and clay thickeners such as bentonite, from the perspective of coatability, storage stability, suppression of pigment sedimentation, and the like.

The viscosity of the hair dye at 25° C. (cone plate viscometer: 50 rpm) is 1.0 to 200 mPa·s, preferably 1.0 to 50 mPa·s, more preferably 4.0 to 10.0 mPa·s, for proper viscosity, dye dissolution stability, imparting smoothness, suppleness, and moist feel to the hair to improve the touch, improving water resistance, further improving usability and coatability when the hair dye is used in an applicator, and application to the hair.

The viscosity range (1.0 to 200 mPa·s) can be modified by suitably modifying the amounts of the components used, the type of the thickener preferably used, as described above, and the amount thereof, and the like.

By setting the viscosity of the hair dye to 1.0 mPa·s or greater, liquid leakage from a container or the like is unlikely to occur. Further, the hair dye is unlikely to adhere to the scalp, and does not soil the clothing. On the other hand, by setting the viscosity to 200 mPa·s or less, a user easily controls the amount of the liquid entangled with the applicator such as a brush, and can uniformly coat the hair dye to the hair.

The hair dye of the present embodiment can be prepared by an ordinary method, and a hair dye having preferable viscosity range and pH range as described above can be manufactured by blending components such as the pigment dispersion liquid for cosmetics containing Red No. 228, resin, lower alcohol, hair dyeing aid, pH modifier and water as described above, within the content ranges as described above and further homogeneously stirring and mixing components with a suitable kneader or the like.

For example, the target hair dye can be prepared by stirring a resin, an alcohol phase such as a lower alcohol, and a colorant containing Pigment Red 4 (C.I. 12085), and an aqueous phase such as water with a general purpose disperser or the like until homogeneous, mixing the alcohol phase and the aqueous phase, further adding a pH modifier, a thickener, and the like, stirring the components with a disperser or the like until homogeneous, and then stirring the components with a homomixer or the like.

When the thus-configured hair dye of the present embodiment is used, a general purpose hair applicator can be used.

The shape, structure, and the like of the hair applicator used are not particularly limited, and examples thereof include an applicator provided with a knock valve applicator, a hair mascara applicator, a tube applicator, and an applicator provided with a piston pressing mechanism.

The thus-configured hair dye of the present embodiment contains, at least, the pigment dispersion liquid for cosmetics containing Pigment Red 4 (C.I. 12085), resin, lower alcohol, hair dyeing aid, pH modifier, and water as described above, and thus has excellent dispersibility of Pigment Red 4 (C.I. 12085) and aging stability. Therefore, a hair dye that ensures stable dispersion of the coloring component thereof, has excellent storage stability, water resistance, usability, coatability, low temperature stability, drying property, low irritation, and the like can be obtained.

EXAMPLES

Next, the present invention will be described in further detail with reference to examples and comparative examples, however, the present invention is not limited to the following examples and the like.

Example 1 to 12 and Comparative Example 1 to 4

Preparation of Pigment Dispersion Liquid for Cosmetics

A pigment dispersion liquid for cosmetics was prepared by dispersing a pigment with each of the blending formulations indicated in Table 1 below in a bead mill.

For each of the obtained pigment dispersion liquids for cosmetics of Example 1 to 12 and Comparative Example 1 to 4, the particle diameter and aging stability were evaluated by the following evaluation method.

These evaluation results are indicated in Table 1 below.

(Measurement of Particle Diameter of Pigment Dispersion Liquid for Cosmetics)

For each of the obtained pigment dispersion liquids for cosmetics, the particle diameter (histogram average particle diameter based on the scattered light intensity distribution: $D_{50}$) was measured at 25° C. with a particle counter [FPAR-1000 (manufactured by Otsuka Electronics Co., Ltd.)].

(Aging Stability: 50° C., after 1 Month)

Each of the obtained pigment dispersion liquids for cosmetics was contained in a glass storage container with a lid, allowed to stand at 50° C. for 1 month, and then evaluated on the basis of the following evaluation criteria.

Evaluation Criteria:

A: The particle diameter is 200 nm or less, and the pigment dispersion liquid is stable (dispersion is homogeneous and stable without sedimentation or aggregation).

B: The particle diameter exceeds 200 nm at the initial stage. Or, the particle diameter increases over time.

C: Gelated.

TABLE 1

| | (Total 100% by mass) Example | | | | | | | | |
|---|---|---|---|---|---|---|---|---|---|
| | 1 | 2 | 3 | 4 | 5 | 6 | 7 | 8 | 9 |
| Water (Purified water) | 54.10 | 54.10 | 54.10 | 54.10 | 54.10 | 77.09 | 66.68 | 55.76 | 54.09 |
| Ethanol | 27.20 | 4.20 | 4.20 | 4.20 | 4.20 | 4.16 | 8.33 | 28.00 | 27.16 |
| Propanol | | 23.00 | | | | | | | |
| Propylene glycol | | | 23.00 | | | | | | |
| Ethylene glycol | | | | 23.00 | | | | | |
| Isopropanol | | | | | 23.00 | | | | |
| Pigment Red 4 (C.I. 12085: Red No. 228) | 12.50 | 12.50 | 12.50 | 12.50 | 12.50 | 12.50 | 12.50 | 12.50 | 12.50 |
| 70% Pigment Yellow 1 (C.I. 11680: Yellow No. 401) Barium sulfate | | | | | | | | | |
| (Methacryloyl ethylbetaine / acrylates) copolymer | 6.20 | 6.20 | 6.20 | 6.20 | 6.20 | 6.25 | 12.49 | 3.74 | 6.25 |
| Polyquaternium-55 *1 | | | | | | | | | |
| (VP/Acryl DMAPA) copolymer *2 | | | | | | | | | |
| water/total solvents | 0.67 | 0.67 | 0.67 | 0.67 | 0.67 | 0.95 | 0.89 | 0.67 | 0.67 |
| Particle diameter [nm] | 142 | 178 | 181 | 188 | 195 | 169 | 198 | 175 | 153 |
| Aging stability [50° C., after 1 month, Upper row: particle diameter (nm), Lower row: evaluation] | 138 A | 174 A | 195 A | 192 A | 189 A | 177 A | 189 A | 181 A | 160 A |

TABLE 1-continued

| | (Total 100% by mass) | | | | | | |
|---|---|---|---|---|---|---|---|
| | Example | | | Comparative Example | | | |
| | 10 | 11 | 12 | 1 | 2 | 3 | 4 |
| Water (Purified water) | 24.29 | 55.30 | 40.50 | 14.56 | 44.09 | 60.00 | 60.00 |
| Ethanol | 56.96 | 37.20 | 22.00 | 69.20 | 37.16 | 30.00 | 30.00 |
| Propanol | | | | | | | |
| Propylene glycol | | | | | | | |
| Ethylene glycol | | | | | | | |
| Isopropanol | | | | | | | |
| Pigment Red 4 (C.I. 12085: Red No. 228) | 12.50 | 2.50 | 30.00 | 12.50 | | 8.0 | 8.0 |
| 70% Pigment Yellow 1 (C.I. 11680: Yellow No. 401) Barium sulfate | | | | | 12.50 | | |
| (Methacryloyl ethylbetaine / acrylates) copolymer | 6.25 | 5.00 | 7.50 | 3.74 | 6.25 | | |
| Polyquaternium-55 *1 | | | | | | 2.00 | |
| (VP/Acryl DMAPA) copolymer *2 | | | | | | | 2.00 |
| water/total solvents | 0.30 | 0.60 | 0.65 | 0.17 | 0.54 | 0.67 | 0.67 |
| Particle diameter [nm] | 185 | 122 | 171 | 288 | gelation | gelation | gelation |
| Aging stability [50° C., after 1 month, Upper row: particle diameter (nm), Lower row: evaluation] | 191 A | 119 A | 179 A | 352 B | gelation C | gelation C | gelation C |

*1: Polymer of quaternary ammonium salt obtained from the reaction of vinylpyrrolidone, dimethylaminopropyl methacrylamide, with (methacrylamido)propyl lauryldimmonium chloride
*2: Copolymer of vinylpyrrolidone with dimethylaminopropyl acrylamide or dimethylaminopropyl methacrylamide As is clear from the results in Table 1 above, Examples 1 to 12 of the present invention were confirmed to be satisfactory in particle diameters and were excellent in both dispersibility and aging stability, as compared with Comparative Examples 1 to 4 out of scope of the present invention.

Example 13 to 18 and Comparative Example 5

Preparation of Hair Dye

Using each of the pigment dispersion liquids for cosmetics obtained above, a hair dye was prepared by stirring components with each of the blending formulations indicated in Table 2 below.

For each of the obtained hair dyes, the particle diameter and aging stability were measured by the measurement method described above, and the viscosity, pH, dyeing property, and drying property were evaluated according to the following evaluation methods.

These results are indicated in Table 2 below.
(Method for Measuring Viscosity)

For each of the hair dyes of Example 13 to 18 and Comparative Example 5 obtained, the viscosity at 25° C. (viscosity measured with a cone plate viscometer: 50 rpm) was measured by the method described above.
(Method for Measuring pH)

For each of the hair dyes of Example 13 to 18 and Comparative Example 5 obtained by the method described above, the pH at 25° C. was measured with a glass electrode pH meter.
(Method for Evaluating Dyeing Property)

Each of the obtained hair dyes (0.2 g) was applied to a human hair bundle (10 cm, 1 g) using a brush, and then dried at room temperature, and sensory evaluation of the dyeing state was made based on the following evaluation criteria.
Evaluation Criteria:
  A: Dyed well, and dyeing is maintained.
  B: Not dyed well, but not uneven in color.
  C: Dyed poorly, or uneven in color.
(Method for Evaluating Drying Property)

Each of the obtained hair dyes was applied to a human hair bundle (10 cm, 1 g) using a brush, and then dried at room temperature, and evaluated based on the following evaluation criteria.
Evaluation criteria:
  A: After 5 minutes, no color migration occurs.
  B: Color migration occurs even after a lapse of 5 minutes.

TABLE 2

| | | (Total 100% by mass) | | | | | |
|---|---|---|---|---|---|---|---|
| | | Example | | | | | Comparative Example |
| | | 13 | 14 | 15 | 16 | 17 | 18 | 5 |
| Water (Purified water) | | 52.36 | 27.00 | 71.00 | 49.26 | 17.36 | 82.36 | 52.36 |
| Ethanol | | 35.90 | 61.26 | 17.26 | 35.90 | 70.9 | 5.9 | 35.9 |

TABLE 2-continued

| | (Total 100% by mass) | | | | | | |
| --- | --- | --- | --- | --- | --- | --- | --- |
| | Example | | | | | | Comparative Example |
| | 13 | 14 | 15 | 16 | 17 | 18 | 5 |
| Example 1 (dispersion liquid of pigment) | 7.00 | 7.00 | 7.00 | 7.00 | 7 | 7 | |
| Comparative Example 1 (dispersion liquid of pigment) | | | | | | | 7 |
| Acid Black 1 (C.I. 20470: Black No. 401) | | | | 0.40 | | | |
| Acid Violet 43 (C.I. 60730: Violet No. 401) | | | | 0.30 | | | |
| Acid Orange 7 (C.I. 15510: Orange No. 205) | | | | 0.40 | | | |
| (Methacryloyl ethylbetaine / acrylates) copolymer | 1.20 | 1.20 | 1.20 | 3.20 | 1.2 | 1.2 | 1.2 |
| Propylene glycol | 3.00 | 3.00 | 3.00 | 3.00 | 3 | 3 | 3 |
| Lactic acid | 0.54 | 0.54 | 0.54 | 0.54 | 0.54 | 0.54 | 0.54 |
| water/total solvents | 0.60 | 0.33 | 0.80 | 0.58 | 0.20 | 0.93 | 0.59 |
| Viscosity (25° C., mPa · s) | 4.6 | 4.9 | 4.7 | 3.9 | 4.5 | 4.8 | 4.7 |
| pH (25° C.) | 4.8 | 4.9 | 4.7 | 6.4 | 4.9 | 4.7 | 4.8 |
| Particle diameter [nm] | 135 | 149 | 142 | 155 | 155 | 147 | 302 |
| Aging stability [50° C., after 1 month, Upper row: particle diameter (nm), Lower row: evaluation | 125 A | 154 A | 133 A | 159 A | 215 A | 152 A | 340 B |
| Dyeing property | A | A | A | A | A | A | A |
| Drying property | A | A | A | A | A | B | A |

As is clear from the results shown in Table 2 above, each of the hair dyes of Example 13 to 18 was confirmed to be satisfactory in viscosity and pH, to be satisfactory in particle diameter and excellent in both of dispersibility and aging stability, and also to achieve both excellent dyeing property and excellent drying property, as a hair dye, as compared with the hair dye of Comparative Example 5.

INDUSTRIAL APPLICABILITY

Provided are a pigment dispersion liquid for cosmetics having excellent dispersibility for a pigment of Pigment Red 4 (C.I. 12085) and aging stability, and an aqueous liquid cosmetic using the same, which is suitable for hair dyes.

The invention claimed is:

1. A pigment dispersion liquid for cosmetics, comprising at least water, a water-soluble organic solvent, a pigment of Pigment Red 4 (C.I. 12085), and a (methacryloyl ethylbetaine/acrylates) copolymer, wherein a ratio of the water to total solvents is 30 to 95% by mass.

2. The pigment dispersion liquid for cosmetics described in claim 1, wherein the water-soluble organic solvent is a lower alcohol having 5 or less carbon atoms.

3. The pigment dispersion liquid for cosmetics described in claim 2, wherein the lower alcohol is ethanol.

4. An aqueous liquid cosmetic comprising the pigment dispersion liquid for cosmetics described in claim 1.

5. The aqueous liquid cosmetic described in claim 4, wherein a ratio of the water to total solvents of the aqueous liquid cosmetic is 30 to 95% by mass.

6. The aqueous liquid cosmetic described in claim 5, wherein a lower alcohol having 5 or less carbon atoms is contained besides the water.

7. The aqueous liquid cosmetic described in claim 6, wherein the lower alcohol is ethanol.

8. An aqueous liquid cosmetic comprising the pigment dispersion liquid for cosmetics described in claim 2.

9. The aqueous liquid cosmetic described in claim 8, wherein a ratio of the water to total solvents of the aqueous liquid cosmetic is 30 to 95% by mass.

10. The aqueous liquid cosmetic described in claim 9, wherein a lower alcohol having 5 or less carbon atoms is contained besides the water.

11. The aqueous liquid cosmetic described in claim 10, wherein the lower alcohol is ethanol.

12. An aqueous liquid cosmetic comprising the pigment dispersion liquid for cosmetics described in claim 3.

13. The aqueous liquid cosmetic described in claim 12, wherein a ratio of the water to total solvents of the aqueous liquid cosmetic is 30 to 95% by mass.

14. The aqueous liquid cosmetic described in claim 13, wherein a lower alcohol having 5 or less carbon atoms is contained besides the water.

15. The aqueous liquid cosmetic described in claim 14, wherein the lower alcohol is ethanol.

* * * * *